(12) United States Patent
Volgas et al.

(10) Patent No.: US 7,659,229 B2
(45) Date of Patent: Feb. 9, 2010

(54) HERBICIDE FORMULATION CONTAINING HEXAZINONE

(75) Inventors: Greg Volgas, Bartlett, TN (US); Johnnie R. Roberts, Memphis, TN (US); Trey Baker, Horn Lake, MS (US)

(73) Assignee: Helena Holding Company, Memphis, TN (US)

( * ) Notice: Subject to any disclaimer, the term of this patent is extended or adjusted under 35 U.S.C. 154(b) by 432 days.

(21) Appl. No.: 11/092,093

(22) Filed: Mar. 29, 2005

(65) Prior Publication Data

US 2005/0227872 A1    Oct. 13, 2005

Related U.S. Application Data

(60) Provisional application No. 60/560,193, filed on Apr. 7, 2004.

(51) Int. Cl.
*A01N 25/02* (2006.01)
*A01N 25/00* (2006.01)
*A01N 33/04* (2006.01)
*A01N 33/00* (2006.01)
*A01N 25/30* (2006.01)
*A01N 25/24* (2006.01)
*A01N 25/22* (2006.01)
*A01N 33/06* (2006.01)

(52) U.S. Cl. .................................................. 504/116.1
(58) Field of Classification Search ............... 504/116.1
See application file for complete search history.

(56) References Cited

U.S. PATENT DOCUMENTS

| | | | | |
|---|---|---|---|---|
| 5,071,463 A | * | 12/1991 | Narayanan et al. | 504/365 |
| 5,178,795 A | | 1/1993 | Roberts | |
| 5,234,919 A | | 8/1993 | Roberts | |
| 5,393,791 A | | 2/1995 | Roberts | |
| 5,580,567 A | | 12/1996 | Roberts | |
| 5,725,630 A | | 3/1998 | Roberts et al. | |
| 5,741,502 A | | 4/1998 | Roberts | |
| 5,877,112 A | | 3/1999 | Roberts et al. | |
| 5,906,961 A | | 5/1999 | Roberts et al. | |
| 6,444,618 B1 | * | 9/2002 | Aven et al. | 504/317 |
| 6,566,308 B1 | * | 5/2003 | Aven | 504/347 |
| 7,297,660 B2 | * | 11/2007 | Stridde et al. | 504/206 |

OTHER PUBLICATIONS

DuPont Velpar® L herbicide ". . . A Growing Partnership With Nature", E.I. du Pont de Nemours and Company, Agricultural Products, Wilmington, Delaware 19898 (1998).

* cited by examiner

*Primary Examiner*—Johann R Richter
*Assistant Examiner*—Courtney Brown
(74) *Attorney, Agent, or Firm*—Connolly Bove Lodge & Hutz LLP

(57) ABSTRACT

A herbicidal composition containing hexazinone and an alkylene carbonate.

24 Claims, No Drawings

HERBICIDE FORMULATION CONTAINING HEXAZINONE

RELATED APPLICATIONS

This application claims benefit to provisional application Ser. No. 60/560,193, filed Apr. 7, 2004 which is incorporated by reference in its entirety for all useful purposes.

BACKGROUND OF THE INVENTION

Prior Art

Hexazinone is a commonly used agricultural and forest management herbicide. Commercial formulations of this product are currently available in liquid forms. One such liquid formulation of hexazinone is VELPAR® L is from du Pont. This formulation uses 40-45% ethanol to dissolve the hexazinone. Ethanol can lower the freeze point of such formulations, but it also makes the products flammable. This is a safety concern for many end users and even distributors. Furthermore, ethanol does not sufficiently lower the freezing point of the formulation to acceptable levels. The Material Safety Data Sheet ("MSDS") for VELPAR® L still requires that the product not be stored for prolonged periods below 32 degrees F. Since VELPAR® L is often used and stored in temperatures below freezing, this formulation problem requires heated storage areas.

Dry formulations of hexazinone have also been commercialized. These dry formulations are typically difficult to mix with other components (i.e. fertilizers, other pesticides, micronutrients, etc.) of spray mixtures. Furthermore, most end-users find measuring liquids much easier than measuring dry products.

Alkylene carbonates have been used to formulate pesticide products. These formulations typically require a non-polar co-solvent to improve solubility of the pesticide active. One such formulation is described by Aven, et. al., U.S. Pat. No. 6,444,618 ("'618 patent"). The '618 patent requires the use of at least one pesticidal crop protection active compound, at least one non-polar organic solvent, an emulsifying surfactant system enabling an oil-in-water emulsion to be formed when the formulation is added to water, and at least one defoaming or foam breaking agent selected from the group consisting of perfluoroalkylphosphonic acids, perfluoroalkylphosphinic acids and perfluoroaliphatic polymeric esters. Optionally, the patent includes the use of "at least one polar aprotic cosolvent", and lists alkylene carbonates as likely candidates. The herbicides include numerous candidates of which one is hexazinone. The '618 patent requires a specific defoaming or foam breaking agent selected from the group consisting of perfluoroalkylphosphonic acids, perfluoroalkylphosphinic acids and perfluoroaliphatic polymeric esters.

Alkylene carbonates are commercially available from Hunstman under the trade names:
JEFFSOL®—ethylene carbonate,
JEFFSOL®—propylene carbonate,
JEFFSOL®—butylene carbonate,
JEFFSOL®—glycerine carbonate.

These products have been promoted as solvents for use in agricultural pesticide formulations. Their typical flash points are between 275 and 320° F., well above the temperature which would require formulations to be labeled as flammable.

SUMMARY OF THE INVENTION

What we have surprisingly discovered is that the alkylene carbonates are especially good solvent systems for hexazinone formulations. The use of these carbonates produces formulations which are both freeze stable down to 15° F. and non-flammable.

The invention further relates to a herbicidal concentrate which comprises hexazinone and at least one carbonate. The concentrate is preferably liquid.

Whenever the term "% by weight" is used in the specification, it is understood that it means percent of the component per the total weight of the composition unless otherwise specified.

The invention can be used without the required defoaming or foam breaking agents described in the '618 patent which are selected from the group consisting of perfluoroalkylphosphonic acids, perfluoroalkylphosphinic acids and perfluoroaliphatic polymeric esters. However, the formulation according to the invention can use alternate foam control agents, such as, but not limited to silica based defoamers.

DETAILED DESCRIPTION OF THE INVENTION

The preferred formulation contains at least 5%, preferably at least 10%, more preferably at least 15% and even more preferably at least 20% and most preferably at least 25% by weight of hexazinone based on the total weight of the composition. The preferred formulation is a liquid concentrate that contains between 1 and 40% more preferably 20-30%, and most preferably 25-30% by weight based of hexazinone based on the total weight of the composition.

The preferred formulation does not require the use of nonpolar organic solvents, emulsifying surfactants or defoaming agents. It may also optionally include any of these components. Again, these ingredients can be present or optional.

The present invention requires a major amount of alkylene carbonate. A major amount is considered of alkylene carbonate Preferably said alkylene carbonate would be selected from the butylenes, ethylene, propylene or glycerin carbonates. Most preferably, the alkylene carbonate is butylene carbonate. Mixtures of alkylene carbonates are also useful.

The amount of alkylene carbonate is the present invention is from 10-99% by weight. More preferably, the invention would contain between 50-80% by weight alkylene carbonate. Most preferably, the invention would contain between 70-80% by weight alkylene carbonate.

The present invention will benefit greatly from the addition of surfactants to improve the spreading and wetting of spray droplets on plant surfaces. The useful surfactants would have as their properties the ability to lower surface tension below 60 dynes/nM when used in water at 1.0% or less.

Useful surfactants or solvents include but are not limited to:
Alcohol alkoxylates including but not limited to:
Based on branched and linear alcohols
Those containing ethylene oxide or propylene oxide
Alcohol alkoxylate sulfates,
Alkylphenol alkoxylates including but not limited to:
Nonylphenol and octylphenols.
Those containing ethylene oxide or propylene oxide
Alkanolamides,
Alkylaryl sulfonates,
Amine oxides,
Amines including but not limited to:
Fatty amine alkoxylates such as but not limited to tallowamine alkoxylates,
Betaine derivatives,
Block polymers of ethylene and propylene glycol,
Carboxylated alcohol or alkylphenol alkoxylates,
Diols, including but not limited to Butanediols, Diphenyl sulfonate derivatives,
Ethers, including but not limited to
Butyl celluslove,
Butyl carbitol,
Ethoxylated amines,
Ethoxylated fatty acids,
Ethoxylated fatty esters and oils,
Ethylene carbonate,
Fatty esters,
Glycerol esters,
Glycols including but not limited to
Propylene glycol,
Ethylene glycol,
Dipropylene glycol,
Diethylene glycol,
Phosphate ester surfactants including but not limited to
Phosphate esters of alcohol alkoxylates,
Phosphate esters of alkylphenol alkoxylates,
Propylene Carbonate,
Sarcosine derivatives,
Silicone-based surfactants,
Sorbitan derivatives including but not limited to:
Sorbitan esters,
Alkoxylated sorbitan esters,
Sucrose and glucose derivatives including but not limited to:
Alkylpolyglucosides,
Sulfates and sulfonates of alkoxylated alkylphenols,
Sulfates of alcohols,
Tristyrylphenol Alkoxylates,
Other surfactants are disclosed in McCutcheon's Emulsifiers and Detergents, North American Edition, 2000.

The formulations may also contain oil-based components. The oil or oil substitutes include, but are not limited to:
Alkylated fatty acid esters, include but are not limited to:
Methylated fatty acids, include but not limited to:
Methylated C6-C19 fatty acids,
Methylated Tall oil fatty acids,
Methylated Oleic acid,
Methylated Linoleic acid,
Methylated Linolenic acid,
Methylated Stearic acid,
Methylated Palmitic acid,
And blends thereof;
Ethylated fatty acids, include but are not limited to:
Ethylated C6-C19 fatty acids,
Ethylated Tall oil fatty acids,
Ethylated Oleic acid,
Ethylated Linoleic acid,
Ethylated Linolenic acid,
Ethylated Stearic acid,
Ethylated Palmitic acid,
And blends thereof;
Butylated fatty acids, include but are not limited to:
Butylated C6-C19 fatty acids,
Butylated Tall oil fatty acids,
Butylated Oleic acid,
Butylated Linoleic acid,
Butylated Linolenic acid,
Butylated Stearic acid,
Butylated Palmitic acid,
And blends thereof;
Alkylated natural oils, include but are not limited to:
Alkylated soybean oil, include but limited to:
Methylated soybean oil,
Ethylated soybean oil,
Butylated soybean oil,
And blends thereof;
Alkylated canola oil, include but are not limited to:
Methylated canola oil,
Ethylated canola oil,
Butylated canola oil,
And blends thereof;
Alkylated coconut oil, include but are not limited to:
Methylated coconut oil,
Ethylated coconut oil,
Butylated coconut oil,
And blends thereof;
Alkylated sunflower oil, include but are not limited to:
Methylated sunflower oil,
Ethylated sunflower oil,
Butylated sunflower oil,
And blend thereof;
Hydrocarbon oils include but are not limited to:
Mineral oils, including but are not limited to:
Paraffinic mineral oils,
Naphthenic mineral oils,
Aromatic mineral oils,
And blends thereof;
Vegetable oils, include but are not limited to:
Soybean oil,
Canola oil,
Cottonseed oil,
And blends thereof;
Fatty acids, include but are not limited to:
C6-C19 fatty acids,
Tall oil fatty acids,
Oleic acid,
Linoleic acid,
Linolenic acid,
Stearic acid,
Palmitic acid,
And blends thereof;
Polybutenes
Epoxified seed oils include but are not limited to:
Epoxified soybean oil and
Other oils or oil substitutes The formulation can contain at least one of the above oils or its equivalent. The oil can also be a blend of at least two oils. When an oil is used, a surfactant or emulsifier must also be used if the composition is intended for aqueous based sprays.

The present invention does not require surfactants (emulsifiers) to mix with water. The addition of surfactants is optional.

Other herbicides that will work include one or more herbicidal compounds selected from the group consisting of chloramben, chlorthal, dicamba, naptalam, 2,3,6-TBA, clopyralid, diflufenzopyr (SAN 835 H), dithiopyr, picloran, thiazopyr (MON 13200), quinclorac, quinmerac, indanofan (MK-243), benazolin, chlorflurenol, dalapon, endothal, flamprop, flamprop M, flupropanate, flurenol, TCA-sodium, bromobutide, chlorthiamid, diflufenican, diphenamid, ethabenzanid (HW 52), isoxaben, mefenacet, monalide, pentanochlor, propanil, propyzanide, tebutam, fluthiamide (BAY FOE 5043), clodinafop, clomeprop, cyhalofop-butyl (XDE-537), 2,4-D, 2,4-DB, dichlorprop, dichlorprop-P, diclofop, fenoxaprop, fenoxaprop-P, fluazifop, fluazifop-P, fluroxypyr, haloxyfop, haloxyfop-P-methyl, isoxapyrifop, MCPA, MCPA-thioethyl, MCPB, mecoprop, mecoprop-P, naproanilide, napropamide, propaquiazfop, quizalofop, quizalofop-P, triclopyr, UBI-C474, bromofenoxim, bromoxynil, dichlobenil, ioxynil, diquat, paraquat, asulam, butylate, carbetamide, chlorbufam, chlorpropham, cycloate, desmedipham, dimepiperate, EPTC, esprocarb, molinate, orbencarb, pebulate, phenmedipham, propham, prosulfocarb, pyributicarb, thiobencarb, tiocarbazil, tri-allate, vernolate, alloxydim, butroxydim, clethodim, cylcoxydim, sethoxydim, sulcotrione, tralkoxydim, acetochlor, alachlor, butachlor, butenachlor, diethatyl, dimethachlor, dimethenamid, metazochlor, metolachlor, pretilachlor, propachlor, propisochlor, tenylchlor (NSK-850), acifluorfen, aclonifen, bifenox, chlomethoxyfen, chlonitrofen, athoxyfenethyl (RC-252), fluoroglycofen, fluoronitrofen, fomesafen, fuiryloxyfen, lactofen, AKH-7088, oxyfluorfen, benfluralin, butralin, dinitramide, ethalfluralin, fluchloralin, isopropalin, oryzalin, pendimethalin, prodiamine, trifluralin, dinoseb, dinoseb acetate, dinoterb, amitrole, benfuresate, bentazone, benzofenap, cafenstrole (CH-900), carfentrazone-ethyl (F-8426), chloridazon, cinmethylin, clomazone, difenzoquat, ethofumesate, pyraflufen-ethyl (ET-751), flumichlorac-pentyl, flumioxazin, flumipropin, flupoxam, fluridone, flurochloridone, flurtamone, fluthiacet methyl (KIH-9201), isoxaflutone (RPA 201772), methazole, nipyraclofen, norflurazon, oxadiargyl, oxadiazon, oxaziclomefone (MY-100), pentoxazone (KPP-314), pyruzolynate, pyrazoxyfen, pyridate, sulfentrazone, (F6285), thidiazimin, anilofos, bensulide, bilanafos, butamifos, fosamine, glufosinate, glyphosate, LS830556, piperophos, imazamethabenz, imazamethipyr (AC-263,222), imazamox (AC-299,263), imazapyr, imazaquin imazethapyr, bispyribac-sodium (KHI-2023), pyribenzoxim (LGC-40863), pyriminobac-methyl (KIH-6127), pyrithiobac-sodium (KIH-2031), tioclorim, cloransulam-methyl (XDE-565), diclosulam (XDE-564), flumetsulam (DE-498), metosulam (XDE-564), flumetsulam (DE-498), metosulam (DE-511), amidosulfuron, azimsulfuron (DPX-A8947), bensulfuron, chlorimuron, chlorsulfliron, cinosulfuron, cyclosulfamuron (AC-322,140), etha-metsulfuron-methyl (DPX-A7881), ethoxysulfuron (HOE 095404), flazasulfuron, flupyrsulfuron (DPX-KE459), halosulfuron (NC-319), imazosulfuron, metsulfuron, NC-300, nicosulfuron, oxasulfuron (CGA-277476), primisulfuron, prosulfuron (CGA-152005), pyrazolsulfuron, rimsulfuron, sulfometuron (DPX-5648), sulfosulfuiron (MON-37500), thifensulfuron, triasulfuron (CGA-121036), tribenuron, triflusulfuron-methyl (DPX-66037), ametryn, atrasin, aziprotryne, cyanazine, desmetryn, dimethame-tryn, dipropetryn, eglinazine, methoprotryne, proglinazine, prometon, prometryne, propazine, simazine, simetryn, terbumeton, terbuthylazine, terbutryn, triaziflam (IDH-1105), trietazine, SMY-1500, hexazinone, metamitron, metribuzin, bromacil, lenacil, terbacil, benzthiazuron, chlorbromuron, chloroxuron, chlorotoluron, cumyluron (JC-940), daimuron, difenoxuron, dimefuron, 1-diuron, ethidimuron, fenuron, fluometuron, isoproturon, isouron, linuron, methabenzthiazuron, methyldymron, metobenzuron, metobromuron, metoxuron, monolinuron, neburon, siduron, tebuthiuron, thiazafluoron, isopropazol (JV 485), KPP 300, KPP 421, BAY YRL 2388, DPXT 5975, azafenidin.

Additional hebicides that will work are disclosed in The Pesticide Manual published by the British Crop Protection Council.

The following patents and reference, which include several ingredients that can be used according to this invention, are incorporated by reference in its entirety for all useful purposes:

U.S. Pat. No. 5,741,502 entitled Homogeneous, essentially nonaqueous adjuvant compositions with buffering capability U.S. Pat. No. 5,725,630 entitled Dry granular fertilizer blend and a method of fertilizing plants U.S. Pat. No. 5,580,567 entitled Homogeneous, essentially nonaqueous adjuvant compositions with buffering capability U.S. Pat. No. 5,393,791 entitled Homogeneous, essentially nonaqueous adjuvant compositions with buffering capability U.S. Pat. No. 5,234,919 entitled Water soluble, highly active dimethoate formulations in an alcohol/ester solvent system U.S. Pat. No. 5,178,795 entitled Homogeneous, essentially nonaqueous adjuvant compositions with buffering capability U.S. Pat. No. 5,906,961 entitled Alkanolamide spreader-sticker surfactant combination U.S. Pat. No. 5,877,112 entitled Agricultural formulation.

These formulations are typically concentrates. Typical use of these formulations would include further dilution in water or oil used as carriers. The amount of dilution would be from about 2 to about 8 quarts per acre of the concentrate and about 1 to about 100 gallons of water per acre. The formulation maybe diluted as disclosed in duPont's VELPAR L® product information ©1998 E.I. du Pont de Nemours and Company, Agricultural Products, Wilmington, Del. which is incorporated by reference in its entirety.

Examples of the inventive concentrate compositions include:

EXAMPLE 1

| | |
|---|---|
| Propylene carbonate | 75.0% |
| Hexazinone technical (98%) | 25.0% |

EXAMPLE 2

| | |
|---|---|
| Butylene carbonate | 75.0% |
| Hexazinone technical (98%) | 25.0% |

EXAMPLE 3

| | |
|---|---|
| Ethylene carbonate | 75.0% |
| Hexazinone technical (98%) | 25.0% |

EXAMPLE 4

| | |
|---|---|
| Propylene carbonate | 70.0% |
| Hexazinone technical (98%) | 25.0% |
| C11 Alcohol (3EO) Ethoxylate | 5.0% |

EXAMPLE 5

| | |
|---|---|
| Propylene carbonate | 50.0% |
| Hexazinone technical (98%) | 25.0% |
| Nonylphenol (6EO) Ethoxylate | 25.0% |

EXAMPLE 6

| Propylene carbonate | 50.0% |
|---|---|
| Petroleum distillates | 30.0% |
| Hexazinone technical (98%) | 20.0% |

EXAMPLE 7

| Butylene carbonate | 50.0% |
|---|---|
| Methylated soybean oil | 30.0% |
| Hexazinone technical (98%) | 20.0% |

The examples 1, 2 and 4 were placed into a freezer at 12 degrees F. along with a control sample of Velpar L. After at least two days in the freezer, the Velpar L sample crytalized. The crystals did not thaw after sitting at ambient for 24 hours. The example formulations did not freeze at all.

Since most uses of the patented formulations will be when mixed with water, the example formulations were added to water and were found to mix readily with water. In some cases, the formulations appeared to actually dissolve in water and produce clear solutions. In other cases, the formulations formed emulsions which were characterized as micro-emulsions, mini-emulsions or emulsions. (As defined by Milton Rosen in his book "Surfactants and Interfacial Phenomena" 2nd edition.)

Carriers other than water are possible. For instance, fertilizer or oils may be used as carriers.

All of the examples would have flash points greater than 200° F. and would be classified by DOT as non-flammable. The Velpar L formulation has a flash point of 73-77° F. according to the MSDS, and would be classified as a flammable liquid.

The formulations according to the invention can be micro-emulsions, macroemulsions or miniemulsions as defined in Surfactants and Interfacial Phenomena, Milton J. Rosen, John Wiley & Sons 2nd edition (1989) pages 304-336 which is incorporated by reference in its entirety.

All the references discussed in this application are incorporated by reference in their entirety for all useful purposes.

While there is shown and described certain specific structures embodying the invention, it will be manifest to those skilled in the art that various modifications and rearrangements of the parts may be made without departing form the spirit and scope of the underlying inventive concept and that the same is not limited to the particular forms herein shown and described.

We claim:

1. A herbicidal composition comprising hexazinone and an alkylene carbonate with the proviso that the composition does not contain a surfactant.

2. A composition as claimed in claim 1, wherein the alkylene carbonate is propylene carbonate.

3. A composition as claimed in claim 1, wherein the alkylene carbonate is ethylene carbonate.

4. A composition as claimed in claim 1, wherein the alkylene carbonate is butylene carbonate.

5. A composition as claimed in claim 1, wherein the ratio of hexaxinone to alkylene carbonate is at most 1:10.

6. A composition as claimed in claim 1, wherein the ratio of hexaxinone to alkylene carbonate is at most 1:5.

7. A composition as claimed in claim 1, wherein the ratio of hexaxinone to alkylene carbonate is at most 1:2.

8. A herbicidal composition as claimed in claim 1, wherein the hexazinone comprises at least 5% by weight of the total composition.

9. A herbicidal composition as claimed in claim 1, wherein the hexazinone comprises at least 10% by weight of the total composition.

10. A herbicidal composition as claimed in claim 1, wherein the hexazinone comprises at least 15% by weight of the total composition.

11. A herbicidal composition as claimed in claim 1, wherein the hexazinone comprises at least 20% by weight of the total composition.

12. A herbicidal composition as claimed in claim 1, wherein the hexazinone comprises at least 25% by weight of the total composition.

13. A herbicidal composition as claimed in claim 1, wherein the hexazinone comprises at least 30% by weight of the total composition.

14. A method comprising mixing the composition as claimed in claim 1 with water and spraying onto plant foliage.

15. The herbicidal composition as claimed in claim 1, which further has no other solvent.

16. A herbicidal composition as claimed in claim 1, which further comprises another solvent.

17. A herbicidal composition comprising hexazinone and a sufficient amount of alkylene carbonate to completely solubolize the hexazinone with the proviso that the composition does not contain a surfactant.

18. A herbicidal composition as claimed in claim 1 which further comprises another herbicide.

19. A herbicidal composition as claimed in claim 1, wherein the composition does not contain a defoaming or foam breaking agent selected from the group consisting of perfluoroalkylphosphonic acid, perfluoroalkylphosphinic acid and perfluoroaliphatic polymeric ester.

20. A herbicidal composition as claimed in claim 7, wherein the hexazinone comprises at least 20% by weight of the total composition.

21. A herbicidal composition comprising hexazinone and an alkylene carbonate with the proviso that the composition does not form an emulsion.

22. The composition as claimed in claim 21, wherein the ratio of hexaxinone to alkylene carbonate is at most 1:2.

23. The herbicidal composition as claimed in claim 22, wherein the hexazinone comprises at least 30% by weight of the total composition.

24. A herbicidal composition comprising hexazinone and an alkylene carbonate with the proviso that the composition is water miscible.

* * * * *